United States Patent [19]

Schepky et al.

[11] Patent Number: 4,696,815

[45] Date of Patent: Sep. 29, 1987

[54] ANTI-DIABETIC PHARMACEUTICAL FORMS AND THE PREPARATION THEREOF

[76] Inventors: Gottfried Schepky, Ulrich-von-Hutten-Weg 2, Biberach 1, Fed. Rep. of Germany, D-7950; Rolf Brickl, Erlenweg 37, Warthausen, Fed. Rep. of Germany, D-7951; Eckhard Rupprecht, Riedbachstrasse 15, Aulendorf-Tannhausen, Fed. Rep. of Germany, D-7960; Andreas Greischel, Dunantstrasse 5, Biberach 1, Fed. Rep. of Germany, D-7950

[21] Appl. No.: 615,892

[22] Filed: May 31, 1984

[30] Foreign Application Priority Data

Jun. 8, 1983 [DE] Fed. Rep. of Germany ....... 3320582

[51] Int. Cl.$^4$ ............... A61K 31/79; A61K 31/495; A61K 31/47; A61K 31/415
[52] U.S. Cl. ................... 424/80; 514/255; 514/309; 514/378; 514/866
[58] Field of Search ............... 424/80; 514/255, 309, 514/378, 866; 546/141, 142; 544/406

[56] References Cited

U.S. PATENT DOCUMENTS

| | | | |
|---|---|---|---|
| 3,668,215 | 6/1972 | Plumpe et al. | 548/209 |
| 3,669,966 | 6/1972 | Amhrogi et al. | 544/406 |
| 3,708,481 | 1/1973 | Kufter et al. | 514/866 |
| 3,883,648 | 5/1975 | Ross et al. | 424/44 |
| 4,430,399 | 2/1984 | Eistetter et al. | 514/475 |

*Primary Examiner*—Johnnie R. Brown
*Assistant Examiner*—John W. Rollins
*Attorney, Agent, or Firm*—Weissenberger, Hammond & Littell

[57] ABSTRACT

The invention is directed to novel galenic preparation forms for providing an oral anti-diabetic agent having an improved release of active substance and processes for producing these preparation forms. The novel pharmaceutical compositions are characterized in that the onset of the activity and the duration of activity are adapted to the particular needs of diabetics with regard to proper control of the metabolism and the associated proper release of insulin. A basic or acidic excipient in a solvent is added to the anti-diabetic active substance in a quantity such that the active substance is made soluble, and then a solubilizing agent is added. Polyvinyl pyrrolidone is dissolved as carrier in this solution, but the carrier may simultaneously serve as the solubilizing adjuvant. This solution is further processed with other excipients to form corresponding preparation forms.

14 Claims, 1 Drawing Figure

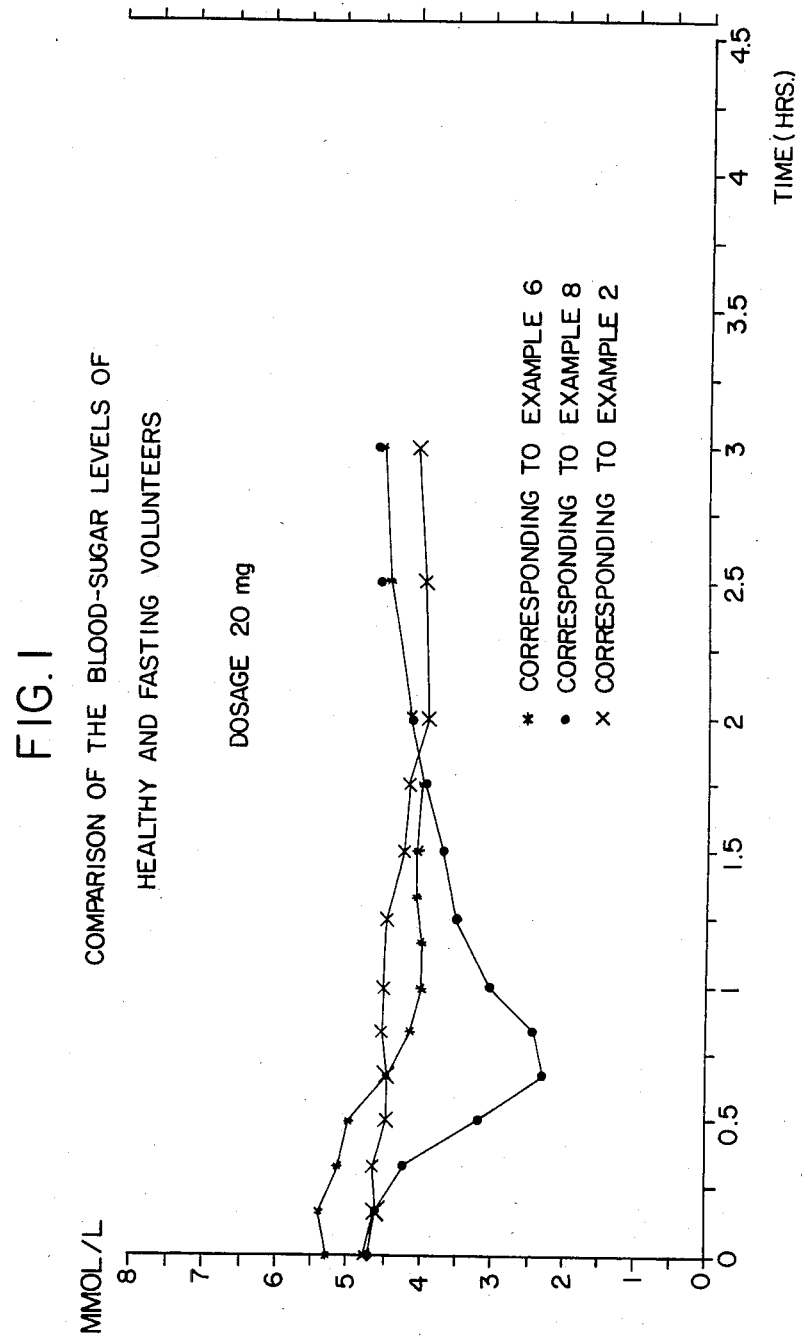

ANTI-DIABETIC PHARMACEUTICAL FORMS AND THE PREPARATION THEREOF

FIELD OF THE INVENTION

This invention relates to novel pharmaceutical forms. More particularly, this invention relates to oral anti-diabetic pharmaceutical forms and the preparation thereof.

BACKGROUND OF THE INVENTION

Generally, in the oral administration of substances which are difficultly soluble in the digestive fluids, such as the anti-diabetic substances mentioned below, the following problems arise: in many cases the active substance can only be partly resorbed, and greatly fluctuating blood levels of the active substance may occur inter- and intra-individually. However, in oral anti-diabetic agents, the start of the activity and the duration of the activity are also of particular importance since the activity should be matched to the blood sugar levels caused by the intake of food. This is not the case with the previously available preparations of anti-diabetic agents in which the effect of the substance and physiological insulin requirements in accordance with the intake of food cannot be reliably matched to one another in terms of time. The activity of the substance often occurs too late: frequently the maximum effect is only achieved at a time at which the blood glucose values are already dropping even without medication after the intake of food. Then the activity of the substance continues even when the blood glucose has returned to its initial level (cf., Berger, in Pelzer and Froesch, Diabetische Enteropathie, Hypoglykämien, Verlag Hans Hüber, Bern-Stuttgart-Wien 1974).

Attempts have been made to synchronize the hypoglycemic activity of a sulfonyl urea with the increase in blood sugar caused by food intake by taking the sulfonyl urea at a suitable time before the meal. However, it was then found that administration of the active substance thirty minutes before the meal did not result in a satisfactory improvement in activity [cf., Sartor et al., Eur. J. Clin. Pharmacolog. 21, 403 to 408 (1982)], partly because of the longer duration of activity mentioned above. Furthermore, a specific time difference between the taking of the medicine and the taking of food can only be reliably monitored in a clinic.

There have also been attempted to solve these problems in the case of substances which are difficultly soluble in the digestive fluids by attempting to optimize the dissolution rate of the active substance difficultly soluble per se in the development of the galenic preparations. This was done, for example, by increasing the surface area of the active substance. Thus, a preparation form is described (German Pat. No. 2,348,334) in which the active substance (also a hypoglycemic substance) is present with a particle surface area of from 3 to 10 $m^2/gm$ in the presence of a wetting agent. However, this objective was also supposed to be achieved by applying the active substance in dissolved form to a substrate or carrier with the largest possible surface area and then eliminating the solvent [cf., H. Rupprecht, Acta Pharm. Technol. 26/1, pages 13 ff (1980)].

Furthermore, attempts have been made to improve the dissolution rate by adding salt forming agents (cf., German Offenlegungsschrift No. 31 24 090.9). However, to improve the solubility and the dissolution rate, solid dispersions were also produced. They consisted of the active substance and one or more water-soluble carriers, possibly combined with surface-active substances. To prepare these dispersions, a homogeneous melt is prepared from the active substance or possibly a salt thereof and a carrier (cf., German Offenlegungsschrift No. 23 55 743). In another process, the active substance and carrier are dissolved in a common solvent, and then the solvent is eliminated. The water soluble carriers used are, inter alia, polyvinyl pyrrolidone or polyethylene glycols [cf., H. R. Merkle, Acta Pharm. Technol. 27/4, pages 193 ff. (1981), and W. L. Chiou, S. Riegelmann, J. Pharm. Sci. 60/9, 1281 ff. (1971)].

If the methods in the literature described below are used to produce preparations containing anti-diabetic substances, a better dissolution rate for the active substance, e.g., gliquidone, is scarcely obtained: the salt formation itself does not result in an increase in the dissolution rate [cf., Table 4, Example 6], and the application of active substance, e.g., gliquidone, to a carrier alone (cf., page 9, line 24 of page 10, line 10 does not produce the desired result either. In corresponding tests, which will be described in more detail hereinafter, the dissolution rate was determined and, in the case of gliquidone, it was found to be no greater than the dissolution rates shown by gliquidone-containing preparations known per se.

OBJECTS OF THE INVENTION

It is an object of the invention to provide novel pharmaceutical forms.

It is also an object of the invention to provide oral anti-diabetic pharmaceutical forms.

It is a further object of the invention to provide a process for preparing said oral anti-diabetic preparations.

These and other objects of the invention will become more apparent in the discussion below.

DETAILED DESCRIPTION OF THE INVENTION

It has now been surprisingly found that preparation forms containing compounds, particularly gliquidone, with a very rapid and total release of the active substance, can be produced by dissolving (a) acidicly reacting active substances by means of basic adjuvants, (b) amphotericly reacting active substances by means of basic or acidic adjuvants, or (c) basicly reacting active substances by means of acidic adjuvants in a solvent in the presence of one or more solubilizing substances comprising polyvinyl pyrrolidone and, optionally, other solubilizing substances. The solution is evaporated to dryness and optionally processed further to form the desired pharmaceutical preparation. The invention also relates to the preparation forms thus obtained. In any case, however, the molar ratio of active substance to basic or acidic excipient must be selected so that there is an excess of basic or acidic excipient.

It is important that sufficient basic or acidic excipient is added to the active substance to ensure rapid and complete dissolution in vivo. This is only possible with a molar ratio of substance to basic or acidic excipient of less than 1:1.

The oral anti-diabetic agents contain as active substances sulfonyl ureas such as gliquidone or substituted phenylcarboxylic acids. Other preferred sulfonyl ureas include glibenclamide, glibornuride, glisoxepide, glipizide, and gliclazide. Gliquidone is 1-cyclohexyl-3-[[p-[2-(3,4-dihydro-7-methoxy-4,4-dimethyl-1,3-dioxo-2-(1H)-isoquinolyl)-ethyl]-phenyl]-sulfonyl]-urea, which has a hypoglycemic effect. However, other anti-diabetic substances which may be used are 4-[2-(aroylamino)-ethyl]-benzoic acids of the formula

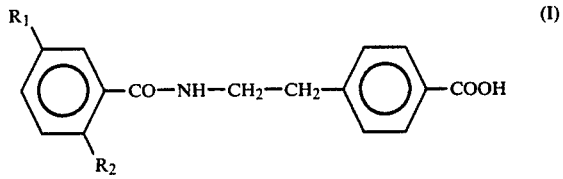
(I)

wherein $R_1$ is a halogen, preferably a chlorine atom, and $R_2$ represents an alkoxy group having from 1 to 3 carbon atoms, preferably a methoxy group, or a piperidin-1-yl or octamethyleneimino group, and also substituted 4-(aralkylaminocarbonylmethyl)-benzoic acids of the formula

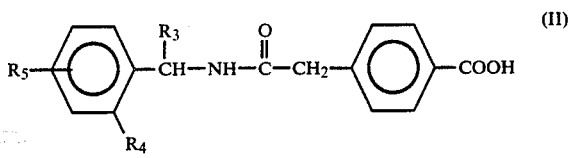
(II)

wherein $R_3$ represents an alkyl group having from 1 to 4 carbon atoms, preferably an n-propyl group, or a phenyl group, $R_4$ represents a piperidin-1-yl, pyrrolidin-1-yl, or hexamethyleneimino group, and $R_5$ represents a hydrogen or halogen atom, preferably a chlorine or fluorine atom, or a methyl or methoxy group. Mixtures of these active substances may also be used.

Micronized gliquidone is contained in a commercially available preparation consisting additionally of corn starch, lactose, and magnesium stearate. This preparation containing gliquidone has already proven satisfactory as a reliable anti-diabetic agent, with the great advantage that it is not contra-indicated when there is restricted kidney function.

To dissolve 2.5 parts by weight of gliquidone, for example, in 50 parts by weight of water, 0.7 parts by weight of ethylenediamine × 1H₂O, 3.0 parts by weight N-methyl-glucamine, or 3.5 parts by weight of diethanolamine are required. If the molar ratios which are absolutely necessary for rapid and complete dissolution of the active substance are compared, the following picture is obtained:

Gliquidone (molecular weight: 527.6): ethylenediamine × H₂O (molecular weight: 78.1) as 1:1.89;
Gliquidone: N-methylglucamine (molecular weight: 195.21) as 1:3.24;
Gliquidone: diethanolamine (molecular weight: 105.14) as 1:7.03; and
Gliquidone: L-lysine (molecular weight: 146.2) as 1:4.33.

This finding cannot be explained by mere salt formation of the gliquidone with the basic excipients in question; it appears that the excess base has an additional stabilizing effect. The same phenomena also apply to the other active substances. This effect was not foreseeable even by someone skilled in the art.

The solutions are prepared with polyvinyl pyrrolidone as solubilizing agent. After evaporation, this substance also acts as carrier at the same time. It is not possible to incorporate the active substance and basic excipient directly in a melt of polyvinyl pyrrolidone since this carrier decomposes even before reaching the melting point.

Suitable basic excipients include a number of inorganic or organic bases which are physiologically harmless, that is, pharmaceutically acceptable, at least in the dosage ranges used, such as sodium hydroxide solution, potassium hydroxide solution, ammonia, tert.sodium phosphate, diethanolamine, ethylenediamine, N-methylglucamine, or L-lysine. The molar ratio of active substance to basic excipient or mixtures of excipients is preferably from about 1:1.1 to 1:10, but a greater excess of base may also be advantageous in some cases.

Suitable acidic excipients include sulfuric and phosphoric acid. The acid must be present in excess.

To stabilize highly concentrated solutions such as those which are clearly obtained when using a preparation according to the invention, it is necessary to add polyvinylpyrrolidone as solubilizing and/or emulsifying substance. Additionally other such substances can be included such as polyoxyethylene polyoxypropylene polymers, polyethylene glycol 4000 or 6000, polyethoxylated sorbitan mono-oleates, sorbitol, glycerol polyethylene glycoloxy stearates, and polyoxyethylene fatty alcohol ethers. Both the nature of the solubilizing substance and also the proportions used are important in determining the dissolution rate of the active substance. The ratio of active substance, e.g., gliquidone, to the total quantity of solubilizing substances is from about 1:0.5 to 1:10 (by weight).

The solution of the active substance, basic or acidic excipients, and solubilizing and/or emulsifying substances is prepared primarily using water or other polar solvents such as lower alcohols, e.g., ethanol, isopropanol, ketones such as acetone, or mixtures of these substances with water.

By using the method of solution according to the invention instead of the melting process known from German Offenlegungsschrift No. 23 55 743, incorporated herein by reference, for incorporating the active substance, the non-fusible solubilizing substance polyvinyl pyrrolidone can be processed in molecular dispersion together with the gliquidone or the other active substances.

The solution to the problem described above is surprising for the following reasons:

The methods of incorporation of substances which are difficultly soluble in the digestive fluids, described in the literature and listed hereinafter, do not result in a significant increase in the dissolution rate of the active substance when applied to the production of preparation forms containing the above-mentioned active substances, nor can they improve the dissolution rate found for the commercially available preparations which contain gliquidone. Some relevant testing is described hereinafter. The dissolution rates were determined after five and 30 minutes by the USP XX Paddle Method in 900 ml of McIlvaine Buffer, at pH 7.0, at 37° C. and at 100 rpm. For each measurement, a quantity of preparation corresponding to 40.0 mg of active substance was used, and each measurement was repeated twice. The average was calculated from the results obtained.

To determine the dissolution rate with an increase in the surface area of gliquidone, 30 parts by weight of the active substance was dissolved in 150 parts by weight of methylene chloride, and the solution was applied to 210 parts by weight of a tablet carrier. After drying, the treated tablet carrier was compressed to form tablets, and the dissolution rate of the gliquidone from these tablets was determined: 5% of the active substance dissolved after 5 minutes and 7% dissolved after 30 minutes. In the case of micronized gliquidone with no excipients, 0% dissolved after 5 and 30 minutes. When the micronized gliquidone was compressed to form tablets (see, the comparison form in Example 1), 5.8% of active substance dissolved after 5 minutes and 7.2% after 30 minutes.

No better dissolution rate was obtained by forming gliquidone salts. Five parts by weight of gliquidone were dissolved in an aqueous solution of 1.9 parts by weight of ethylenediamine×H$_2$O, with heating and stirring, the solution was dried in vacuo in a rotary evaporator, and the resulting solid product was passed through a 1.0 mm mesh screen. This product also yielded a quantity of only 4% of dissolved active substance after 5 minutes and 30 minutes.

Not even the use of a gliquidone-containing dispersion produced any better dissolution rates. Analogously to the method described in German Offenlegungsschrift No. 23 55 743, 1.47 parts by weight of gliquidone were dissolved in a melt consisting of 79.1 parts by weight of polyglycol 4000 and 5.0 parts by weight of polyoxyethylene-40-stearate, and then 14.43 parts by weight of potassium bicarbonate were dispersed therein. The solidified melt was rubbed through a screen with a mesh size of 1.0 mm. The measurement of the dissolution rate gave a result of 10% of active substance after 5 minutes and 7% after 30 minutes.

A further series of tests was carried out to check whether the use of gliquidone salts in the process described in German Offenlegungsschrift No. 23 55 743 leads to better dissolution rates. Again, a melt consisting of 79.1 parts by weight of polyethylene glycol 4000 and 5.0 parts by weight of polyoxyethylene-40-stearate was used, in which a saturated solution of the gliquidone salt in question was prepared. Then, 14.43 parts by weight of potassium bicarbonate was dispersed in this solution. The solidified melt was passed through a screen with a mesh size of 1.0 mm.

TABLE 1

| Gliquidone Salt containing | Maximum Active Substance (calculated as base) Soluble in Melt Consisting of PEG 4000 and Polyoxyethylene-40-stearate (%) | Quantity of Solid Solution Required for 30 mg Gliquidone for Each Dose (gm) |
| --- | --- | --- |
| Ethylenediamine | 0.65 | 4.6 |
| NH$_4$OH | 2.40 | 1.25 |
| N—Methyl-glucamine | 0.54 | 5.54 |
| Piperidine | 2.15 | 1.395 |
| NaOH | 1.99 | 1.51 |

(PEG 4000 = polyethylene glycol 4000)

It is easy to see from these results that the quantity of melt required for 30 mg of gliquidone cannot be contained in a disintegrating tablet which can be swallowed. Thus, the process according to German Offenlegungsschrift No. 23 55 743 is unsuitable for gliquidone salts and also for the salts of the other active substances mentioned hereinbefore.

As can be seen from the tests described above, it is not possible to achieve rapid and total dissolution of the active substances, demonstrated on gliquidone, using the known methods which are described as suitable for such purposes.

When pharmaceutical preparations are developed, optimization is carried out using in vitro methods. The release and dissolution of the active substance are determined using dissolution tests. To create conditions comparable to those obtained in vivo, these tests are normally carried out in an acidic medium at pH 1.2 If this pH is used with the forms according to the invention, no measurable release rates are obtained. In vitro dissolution tests must therefore be carried out at pH 7 (or above). This is due to the fact that the solubility of the active substance is no longer sufficient at pH levels below 7. It would therefore be expected that there would be only a slight release of active substance in vivo in the acidic range of the intestinal tract. The rapid and total resorption of the active substance even in the upper region of the intestinal tract is therefore surprising to anyone skilled in the art. It is also surprising that in spite of the difference between the in vivo situation and the measurement of the dissolution rate in vitro, there is considerable agreement between in vitro and in vivo. This is shown by a comparison of the dissolution rates in Example 2 in Table 2 with the curve in FIG. 1, on the other hand, and the curve for the preparation according to Example 2 with the curves for the preparations of Examples 6 and 8, which are not according to the invention.

If the hypoglycemically active substances mentioned above are formulated by the processes described above, pharmaceutical compositions are obtained wherein the action of the active substance is matched to the physiological requirement of the patient for this medicament. These special pharmaceutical products ensure rapid and complete resorption of the active substance. Rapid resorption shortens the time which must elapse between taking of the medicament and taking of a meal to synchronize the hypoglycemic activity of the sulfonyl urea with the increase in blood sugar caused by food intake. Rapid and total resorption reduces intra- and interindividual fluctuations in the blood glucose level, minimizes the dependence of resorption on the state of the gastrointestinal tract or on the nature or quantity of food taken, and thus ensures the correct metabolic pattern and consequently a correct insulin release. The disadvantages described above relating to the forms known at present are avoided by using the process according to the invention.

Trials on humans (see FIG. 1) demonstrated the rapid start of action of the preparation according to the invention (Example 2) and the slight activity of Examples 6 and 8, which are not according to the invention. It is also found that the values found in vitro and in vivo correspond well.

The findings mentioned above show that the medical objectives (a) avoiding a non-physiological rise in blood sugar after intake of food, and (b) avoiding a massive drop in blood sugar some hours after food intake, are achieved with the preparations according to the invention.

The methods of measurement used were as follows:

Determining the Blood Glucose

The blood sugar was measured in whole venous blood. Fifty microliters of blood were freed from protein with 500 μl of 0.32M perchloric acid. After centrifuging, the glucose in the supernatant was measured by the hexokinase method using an automatic substrate.

Human Testing

Blood samples were taken through long-term catheters with heparinized disposable syringes. After a preliminary period of 15 minutes in which the course of the blood sugar level and of the insulin level without any medicament was measured, the galenic preparation was administered in the form of a granulate or in tablet form in the appropriate dosage with 70 ml of water.

The essence of the invention will be investigated more closely hereinafter in a discussion of the results obtained in the tests described in the examples.

Table 2 shows the correlation between the quantity of polyvinyl pyrrolidones and the dissolution rate.

Table 3 shows that the presence of an alkaline excipient is absolutely necessary not only for dissolving gliquidone but also for obtaining rapid release of the active substance. To achieve an equally high dissolution rate solely by using the solubilizing carrier KOLLIDON 25 ® and without using an alkaline excipient, the quantity of KOLLIDON 25 in this example would have to be increased by almost a power of 10. However, such a high proportion of polyvinyl pyrrolidone is impossible for practical reasons—the preparations would no longer be manageable as oral preparations, and in any case, such forms would not be viable from the point of view of manufacture and cost.

The following examples are intended to illustrate the invention and should not be construed as limiting the invention thereto. Moreover, in the examples, the following substances are employed:

AVICEL ®, a microcrystalline cellulose available from FMC Export Corporation Philadelphia Pa/USA;

KOLLIDON 25, a poly-N-vinylpyrrolidone(-2), available from BASF, D-6700 Ludwigshafen (West-Germany):

PLURONIC ® F 68, a polyoxyethylene polyoxypropylene polymer, available from Wyandotte Chemicals Corp., Wyandotte Mich.;

EXPLOTAB ®, a sodium carboxymethyl starch, available from Eastman Kodak Comp. Rochester-/USA;

PEG 4000=polyethylene glycol 4000; and

AMBERLITE ® IRP 88, a potassium salt of polymers of methacrylic acid and divinylbenzene (methacrylic acid polymer with vinylbenzene, potassium salt), available from Rohm and Haas Deutschland GmbH, Philadelphia, PA./USA.

EXAMPLES

Examples 1 to 3

Table 2 contains Examples 1 to 3 with their dissolution rates. The compositions of Examples 1 to 3 each contain 5 mg of gliquidone and 1.9 mg of ethylenediamine×H₂O.

TABLE 2

| Example No. | KOLLIDON 25 (mg) | Dissolution Rate in percent of Active Substance Which Went into Solution | |
|---|---|---|---|
| | | After 5 mins. | After 30 mins. |
| 1 | 10 | 91 | 93 |
| 2 | 30 | 95 | 97 |
| 3 | 60 | 92 | 96 |

The preparation forms in the Examples were prepared as follows:

The basic excipient is dissolved in 100 parts by weight of water at 70° C. with stirring. The active substance is added, and the mixture is stirred until the latter is completely dissolved. Polyvinyl pyrrolidone is dissolved in this solution. The solution is evaporated to dryness in vacuo with stirring, and the product is rubbed through a screen with a mesh size of 1 mm.

A comparison with a known gliquidone-containing preparation of the following composition:

Micronized gliquidone: 30 parts by weight
Corn starch: 75 parts by weight
Lactose: 132 parts by weight
Magnesium stearate: 3 parts by weight
showed by the following dissolution rate:
5.8% of gliquidone after 5 minutes;
7.2% of gliquidone after 30 minutes.

EXAMPLES 4 AND 5

The preparation forms shown in Table 3 below comprise, in addition to 5 mg of gliquidone, increasing quantities of polyvinyl pyrrolidone (KOLLIDON 25) but no basic excipient and no carrier. A useful dissolution rate is achieved only with upwards of 12 times the quantity of KOLLIDON 25.

The preparation forms in these examples were produced by dissolving the active substance and solubilizing substance together in ethanol. The solution was then evaporated to dryness, and the product was rubbed through a screen with a mesh size of 1 mm.

TABLE 3

| Example No. | KOLLIDON 25 (mg) | Dissolution Rate in percent of Active Substance Which Went into Solution | |
|---|---|---|---|
| | | After 5 mins. | After 30 mins. |
| 4 | 10 | 24 | 44 |
| 5 | 60 | 90 | 93 |

EXAMPLES 6 TO 8

The preparation form in Example 7 was prepared as described in Example 1. The preparation forms of Examples 6 and 8 were produced analogously to the method described in Examples 4 and 5.

Table 4 shows the compositions and the dissolution rates measured. As can be seen from Table 4, the presence of a basic excipient alone does not lead to a useful dissolution rate nor does the sole presence of a solubilizing substance (without a basic excipient and a carrier) lead to a product with a useful dissolution rate. This shows that the combination of gliquidone with a basic excipient and solubilizing agent in the presence of a water-insoluble carrier yields the best results in terms of rapid and fullest possible dissolution of the active substance.

TABLE 4

| Example No. | Gliquidone (mg) | Basic Excipient | Solubilizing Agent | Dissolution Rate in percent of Active Substance Which Went into Solution | |
|---|---|---|---|---|---|
| | | | | After 5 mins. | After 30 mins. |
| 6 | 5 | 1.9 mg of Ethylenediamine × H₂O | — | 4 | 4 |
| 7 | 25 | 6.5 mg of Ethylenediamine × H₂O | 30 mg of KOLLIDON 25 | 88 | 94 |
| 8 | 25 | — | 30 mg of KOLLIDON 25 | 12 | 24 |
| 9 | 30 | 36.0 mg of L-lysine | 20 mg of KOLLIDON 25 + 24 mg of PLURONIC F 68 | 91 | — |

EXAMPLE 9

Each tablet has the following composition:

| Component | Amount (mg) |
|---|---|
| Gliquidone | 30.0 |
| L-lysine | 36.0 |
| KOLLIDON 25 | 20.0 |
| PLURONIC F 68 | 24.0 |

Processing is carried out analogously to Examples 1 to 3, but with the solution being evaporated in a spray dryer.

The following are added per tablet:

| | |
|---|---|
| | 105.0 mg AVICEL |
| | 105.0 mg EXPLOTAB |
| TOTAL: | 320.0 mg |

From this mixture round biconvex tablets weighing 320 mg and measuring 10 mm in diameter are compressed and coated with hydroxypropyl methylcellulose to mask the flavor.

Dissolution rate: 91% of gliquidone after 5 minutes.

EXAMPLE 10

Film-coated tablets containing 4-[(1-(2-piperidino-phenyl)-1-butyl)-amino-carbonylmethyl]-benzoic acid (a) Each tablet has the following composition:

| Component | Amount (mg) |
|---|---|
| 4-[(1-(2-Piperidino-phenyl)-1-butyl)-aminocarbonylmethyl]-benzoic acid | 30 |
| AMBERLITE IRP 88 | 134 |
| AVICEL | 134 |
| Magnesium stearate | 2 |
| TOTAL: | 300 |

The tablet components are mixed together, compressed to form round biconvex tablets weighing 300 mg and measuring 10 mm in diameter, and then coated with hydroxypropyl methylcellulose to mask the flavor.

Dissolution rate: 25.6% of active substance after 5 minutes; 36.3% of active substance after 30 minutes.

(b) Granulate of active substance has the following composition:

| Component | Amount (mg) |
|---|---|
| Active substance of Example 10(a) | 30 |
| L-lysine | 36 |
| KOLLIDON 25 | 30 |
| PLURONIC F 68 | 24 |

Processing is carried out analogously to Examples 1 to 3. The following are added to this granulate:

| | |
|---|---|
| | 90 mg AVICEL |
| | 90 mg AMBERLITE IRP 88 |
| TOTAL: | 300 mg |

Round biconvex tablets weighing 300 mg and measuring 10 mm in diameter are compressed from this mixture and coated with hydroxypropyl methylcellulose to mask the flavor.

Dissolution rate: 48,7% of active substance after 5 minutes; 81,3% of active substance after 30 minutes.

EXAMPLE 11

Film-coated tablets containing 4-[N-(α-phenyl-2-piperidino-benzyl)-aminocarbonylmethyl]-benzoic acid (a) Each tablet has the following composition:

| Component | Amount (mg) |
|---|---|
| Active substance | 30 |
| AMBERLITE IRP 88 | 134 |
| AVICEL | 134 |
| Magnesium stearate | 2 |
| TOTAL: | 300 |

The tablet ingredients are mixed together, compressed to form round biconvex tablets weighing 300 mg and measuring 10 mm in diameter, and coated with hydroxypropyl methylcellulose to mask the flavor.

Dissolution rate: 15.8% of active substance after 5 minutes; 20.9% of active substance after 30 minutes.

(b) Granulate of active substance has the following composition:

| Component | Amount (mg) |
|---|---|
| Active substance of Example 11(a) | 30 |
| L-lysine | 30 |
| KOLLIDON 25 | 30 |
| PLURONIC F 68 | 24 |

Processing proceeds analogously to Examples 1 to 3. The following are added to this granulate:

| | |
|---|---|
| | 93 mg AVICEL |
| | 93 mg AMBERLITE IRP 88 |

-continued

| | |
|---|---|
| TOTAL: | 300 mg |

Round biconvex tablets weighing 300 mg and measuring 10 mm in diameter are compressed from this mixture and coated with hydroxypropyl methylcellulose to mask the flavor.

Dissolution rate: 58.4% of active substance after 5 minutes; 93.4% of active substance after 30 minutes.

EXAMPLE 12

Film-coated tablets containing 4-[2-(5-chloro-2-octamethyleneimino-benzoyl-amino)-ethyl]-benzoic acid (a) Each tablet has the following composition:

| Component | Amount (mg) |
|---|---|
| Active substance | 30 |
| AMBERLITE IRP 88 | 134 |
| AVICEL | 134 |
| Magnesium stearate | 2 |
| TOTAL: | 300 |

The tablet ingredients are mixed together, compressed to form round biconvex tablets weighing 300 mg and measuring 10 mm in diameter and then coated with hydroxypropyl methylcellulose to mask the flavor.

Dissolution rate: 18.4% of active substance after 5 minutes; 27.2% of active substance after 30 minutes.

(b) Granulate of active substance has the following composition:

| Component | Amount (mg) |
|---|---|
| Active substance of Example 12(a) | 30 |
| L-lysine | 36 |
| KOLLIDON 25 | 30 |
| PLURONIC F 68 | 24 |

Processing is carried out analogously to Examples 1 to 3.

The following are added to the granulate:

| | |
|---|---|
| | 90 mg AVICEL |
| | 90 mg AMBERLITE IRP 88 |
| TOTAL: | 300 mg |

Round biconvex tablets weighing 300 mg and measuring 10 mm in diameter are compressed from this mixture and coated with hydroxypropyl methylcellulose to mask the flavor.

Dissolution rate: 96.2% of active substance after 5 minutes; 99.9% of active substance after 30 minutes.

The following example describes the production of pharmaceutical preparation forms.

EXAMPLE 13

Capsules

A quantity of granulate from Example 1 corresponding to 10 mg of gliquidone is mixed with a corresponding quantity of corn starch and magnesium stearate. The resulting mixture is then packed into size 5 hard gelatine capsules.

The anti-diabetically active substances useful according to the invention are administered orally, optionally in combination with other active ingredients, in known manner. The daily dose for adults is from about 5 to 150 mg (from about 0,07 to 2 mg/kg of body weight), preferably from about 10 to 120 mg (from about 0,18 to 1,6 mg/kg of body weight), generally administered in the form of several, preferably from 2 to 4, individual doses to achieve the desired results. Dependent upon the type and body weight of the patient to be treated, on the type and severity of the disease, on the type of preparation and on the route of administration as well as on the period or interval over which the administration takes place, it may, however, be necessary to deviate from the above dosages. Thus it may be sufficient in some cases to administer more or less than the above-mentioned amounts of active ingredient. The optimum dosage and route of administration of the active ingredients which are necessary in each case can easily be determined by one skilled in the art.

The compositions prepared according to the invention can be further processed to produce pharmaceutical compositions useful for administration according to the invention. For example, the compositions can be admixed with conventional pharmaceutical excipients to form tablets, coated tablets, capsules, solutions, and the like. Such conventional excipients include for example, microcrystalline cellulose, potassium salt of polymers of methacrylic acid and divinylbenzene, magnesium stearate, lactose corn starch, polyvinylpyrrolidone, gelatine and the like.

The preceding specific embodiments are illustrative of the practice of the invention. It is to be understood, however, that other expedients known to those skilled in the art or discussed herein, may be employed without departing from the spirit of the invention or the scope of the appended claims.

We claim:

1. An oral antidiabetic pharmaceutical composition consisting essentially of a conventional pharmaceutical excipient and the evaporation residue of a solution of an effective antidiabetic amount of an acidic, amphoteric or basic antidiabetic sulfonyl urea, a basic or acidic excipient and polyvinylpyrrolidone in an inert polar solvent, where the molar ratio of sulfonyl urea to basic or acid excipient is less than 1:1 and the ratio of sulfonyl urea to polyvinylpyrrolidone is about 1:0.5 to 1:10 by weight.

2. A composition of claim 1, where said sulfonyl urea is gliquidone, glibenclamid, gliboruride, glisoxepide, glipizide or gliclazide.

3. A composition of claim 1, where said sulfonyl urea is gliquidone.

4. A composition of claim 1, where said basic excipient is sodium hydroxide, potassium hydroxide, ammonia, tert.sodium phosphate, diethanolamine, ethylenediamine, N-methyl-glucamine or L-lysine, and said acidic excipient is sulfuric acid or phosphoric acid.

5. A composition of claim 1, where the molar ratio of sulfonyl urea to basic or acidic excipient is from 1:1.1 to 1:10.

6. A composition of claim 1, wherein said conventional pharmaceutical excipient includes additional solubilizing agent.

7. The method of preparing an oral anti-diabetic pharmaceutical composition containing an antidiabetic sulfonyl urea as the active ingredient, which comprises dissolving (a) an acidic antidiabetic sulfonyl urea with a basic excipient, or (b) an amphoteric antidiabetic sulfonyl urea with a basic or acidic excipient, or (c) a basic antidiabetic sulfonyl urea with an acidic excipient and polyvinylpyrrolidone in an inert polar solvent, where the molar ratio of sulfonyl urea to basic or acidic excipient is less than 1:1 and the ratio of sulfonyl urea to polyvinylpyrrolidone is from about 1:0.5 to 1:10 parts by weight, and evaporating the resulting solution to dryness.

8. The method of claim 7, where said sulfonyl urea is gliquidone, glibenclamid, glibornuride, glisoxepide, glipizide or gliclazide.

9. The method of claim 7, where said basic excipient is sodium hydroxide, potassium hydroxide, ammonia, tert.sodium phosphate, diethanolamine, ethylenediamine, N-methyl-glucamine or L-lysine, and said acidic excipient is sulfuric acid or phosphoric acid.

10. The method of claim 7, which comprises dissolving gliquidone with a basic excipient in an inert polar solvent, where the molar ratio of gliquidone to basic excipient is less than 1:1, dissolving polyvinylpyrrolidone in the resulting solution, the ratio of gliquidone to polyvinylpyrrolidone being about 1:0.5 to 1:10 parts by weight, and evaporating the solution thus obtained to dryness.

11. The method of claim 10 wherein the evaporation residue is combined with a conventional pharmaceutical excipient to produce the desired oral antidiabetic pharmaceutical composition.

12. The method of claim 7, wherein the molar ratio of sulfonyl urea to basic or acidic excipient is about 1:1.1 to 1:10.

13. The method of claim 7, where said conventional pharmaceutical excipient includes an additional solubilizing agent.

14. The method of claim 7, wherein the evaporation residue is combined with a conventional pharmaceutical excipient to produce the desired oral antidiabetic pharmaceutical composition.

* * * * *